United States Patent [19]

Dessau et al.

[11] Patent Number: 4,931,416

[45] Date of Patent: Jun. 5, 1990

[54] THALLIUM OR LEAD-CONTAINING MICROPOROUS CRYSTALLINE MATERIALS AND THEIR USE AS DEHYDROGENATION DEHYDROCYCLIZATION AND REFORMING CATALYSTS

[75] Inventors: Ralph M. Dessau, Edison, N.J.; Ernest W. Valyocsik, Yardley, Pa.

[73] Assignee: Mobil Oil Corporation, New York, N.Y.

[21] Appl. No.: 346,374

[22] Filed: Apr. 28, 1989

Related U.S. Application Data

[62] Division of Ser. No. 210,946, Jun. 24, 1988, abandoned.

[51] Int. Cl.$^5$ .............................................. B01J 29/32
[52] U.S. Cl. ...................................... 502/74; 502/66; 502/71
[58] Field of Search .................. 502/71, 77, 66, 74

[56] References Cited

U.S. PATENT DOCUMENTS

| | | | |
|---|---|---|---|
| Re. 29,948 | 3/1979 | Dwyer et al. | 208/110 |
| 3,702,293 | 11/1972 | Hayes et al. | 208/139 |
| 3,702,294 | 11/1972 | Rausch | 208/139 |
| 3,878,125 | 4/1975 | Mitsche et al. | 502/73 |
| 3,878,131 | 4/0000 | Hayes | 252/466 PT |
| 4,104,320 | 8/1978 | Bernard et al. | 260/673.5 |
| 4,276,151 | 1/1981 | Plank et al. | 208/138 |
| 4,325,808 | 4/1982 | Kim et al. | 208/65 |
| 4,347,394 | 8/1982 | Detz et al. | 585/419 |
| 4,387,258 | 6/1983 | Vadekar et al. | 585/259 |
| 4,394,300 | 7/1983 | Chu et al. | 502/77 |
| 4,416,806 | 11/1983 | Bernard et al. | 502/74 |
| 4,418,006 | 11/1983 | Kim et al. | 502/73 |
| 4,435,283 | 3/1984 | Buss et al. | 208/138 |
| 4,456,527 | 6/1984 | Buss et al. | 208/89 |
| 4,485,185 | 11/1984 | Onodera et al. | 502/71 |
| 4,486,547 | 12/1984 | Imai et al. | 502/223 |
| 4,487,843 | 12/1984 | Telford et al. | 502/85 |
| 4,487,848 | 12/1984 | Robinson et al. | 502/223 |
| 4,547,472 | 10/1985 | Nordstrand | 502/66 |
| 4,576,805 | 3/1986 | Chang et al. | 423/277 |
| 4,588,495 | 5/1986 | Franck et al. | 208/65 |
| 4,604,371 | 8/1986 | Moorehead | 502/60 |
| 4,614,834 | 9/1986 | Lambert et al. | 585/419 |
| 4,619,906 | 10/1986 | Lambert et al. | 502/66 |
| 4,788,169 | 11/1988 | Degman, Jr. et al. | 502/71 |

FOREIGN PATENT DOCUMENTS

| | | |
|---|---|---|
| 0107389 | 4/1984 | European Pat. Off. . |
| 2033358 | 5/1980 | United Kingdom . |
| 2114150 | 8/1983 | United Kingdom . |

OTHER PUBLICATIONS

G. Wengui et al, "IR Study of Framework Vibrations and Surface Properties of High Silica Zeolites", ZEOLITES, Elsevier Science, Amsterdam, 1985, p. 279.

Ione, Journal of Molecular Catalysis, 31, pp. 355–370 (1985).

Ione, Elsevir Science, (1984), pp. 151–158.

Seventh Internation Zeolite Conference, "Preprints of Poster Papers", Japan Association of Zeolite, Tokyo, Japan (Aug. 17–22, 1986), pp. 309–310.

*Primary Examiner*—Carl F. Dees
*Attorney, Agent, or Firm*—Alexander J. McKillop; Charles J. Speciale; Marina V. Schneller

[57] ABSTRACT

Crystalline microporous thallium or lead containing silicate isostructural with zeolites, as catalysts, exhibit high selectivity for dehydrogenation, dehydrocyclization, and reforming.

24 Claims, No Drawings

4,931,416

THALLIUM OR LEAD-CONTAINING MICROPOROUS CRYSTALLINE MATERIALS AND THEIR USE AS DEHYDROGENATION DEHYDROCYCLIZATION AND REFORMING CATALYSTS

This is a division of copending application Ser. No. 210,946, filed on June 24, 1988, now abandoned.

FIELD OF THE INVENTION

Non-acidic crystalline microporous materials containing a modifier comprising thallium or lead are described. As catalyst compositions these materials exhibit high selectivity for catalytic dehydrogenation and/or dehydrocyclization of paraffins.

BACKGROUND OF THE INVENTION

Naturally occurring and synthetic crystalline microporous materials have been demonstrated to exhibit catalytic properties for various types of hydrocarbon conversions. The term "crystalline" used to refer to these materials relates to the ordered definite crystalline structure of the material which is unique and thus identifiable by a characteristic X-ray diffraction pattern.

The term "microporous" as it refers to such material relates to pores, or channels, with diameters of less than 20 Angstroms. Examples of these microporous crystalline materials include crystalline silicates, crystalline alumino-silicates (zeolites), crystalline ALPOs, crystalline SAPO and related compositions and intercalated pillared materials derived from clays, layered silicates and titanates. The crystalline silicate, alumino silicate (zeolites), ALPOS and SAPOs, have pores of uniform size and channel systems which are uniquely determined by unit structure of the material. The uniform pore size and/or channel systems allow such a material to selectively absorb molecules of certain dimensions and shapes. In the art, microporous material having pores, or channels, of less than 20 Angstroms, can be divided into small, medium and large pore by the diameters of those pores, or channels. The pores of the small pore material have an average diameter of less than 5 Angstroms; medium size pores range from an average diameter of about 5 to about 7 Angstroms, and large pore silicates indicates a diameter of greater than about 7. The word "average" is used to refer to diameter to embrace those species in which the pore is elliptical. Alternatively, the demarcation between small, medium, and large pore materials can be based on the following sorption properties (measured at room temperature for crystallites having a minimum dimension of 0.1 micron):

1. Small pore: $n-C_6/i-C_6$ sorption ratio greater than approximately 10.
2. Medium pore: $n-C_6/i-C_6$ is less than 10 and $n-C_6$/Mesitylene sorption ratio greater than approximately 5.
3. Large pore: $n-C_6$/Mesitylene sorption ratio less than approximately 5.

In the art, zeolites are a subclass of crystalline microporous silicates. Zeolites can contain aluminum as well as silicon. In some zeolites, the upper limit of the silicon/aluminum atomic ratio is unbounded. ZSM-5 is one such example wherein the silicon/aluminum atomic ratio is at least 2.5 and up to infinity. By way of illustration, U.S Pat. No. 3,941,871, reissued as RE 29,948, discloses a porous crystalline silicate made from a reaction mixture containing no deliberately added aluminum and exhibiting the X-ray diffraction pattern characteristic of ZSM-5 zeolites.

Zeolites can be acidic or non-acidic, depending on the framework aluminum content and on the amount of compensating cations, such as $Na^+$, $K^+$, etc. ALPOs described in U.S. Pat. No. 4,310,440, which is incorporated by reference herein, are neutral. SAPOs described for example in U.S. Pat. No. 4,440,871, which is incorporated by reference herein, can be acidic or non-acidic depending on the ratio of framework Al:P therein and the compensating cation, such as $Na^+$, $K^+$ (other than proton species and other than proton forming species such as $NH_4^+$). ELAPOs are described in U.S. Pat. No. 4,500,651, while MeAPOs are described in U.S. Pat. Nos. 4,544,143 and 4,567,029, each of said latter three patents being incorporated by reference herein.

SUMMARY OF THE INVENTION

The present invention is directed to new compositions of matter, to methods of production, and to use as a catalyst in paraffin dehydrogenation and paraffin dehydrocyclization. The composition is non-acidic, microporous crystalline material containing a dehydrogenation metal and a modifier which is thallium or lead. It has been discovered that these thallium or lead containing non-acidic crystalline microporous materials containing a dehydrogenation metal exhibit high selectivity for dehydrogenation and/or dehydrocyclization of paraffins. Moreover, while exhibiting that high selectivity for paraffin dehydrocyclization, these compositions exhibit decreased selectivity for hydrogenolysis (especially methane formation) relative to their thallium-free and lead-free counterparts. Furthermore, these compositions are effective reforming catalysts.

DETAILED DESCRIPTION OF THE INVENTION

One aspect of the invention is a catalyst comprising hydrogenation/dehydrogenation metal and a non-acidic crystalline microporous modifier containing material in which the modifier is thallium or lead. As catalysts those compositions exhibit high selectivity for parraffin dehydrogenation and/or dehydrocyclization reactions, under conditions effective for paraffin dehydrogenation and/or dehydrocyclization.

The amount of dehydrogenation metal in the catalyst can range from 0.01 to 30 weight percent and preferably 0.1 to 10 weight percent of the non-acidic crystalline microporous modifier containing material. In a preferred embodiment, platinum is the hydrogenation/dehydrogenation metal. However, the hydrogenation/dehydrogenation metal can be any Group VIII metal including those of the platinum group, chromium and vanadium.

The thallium modifier content of the non-acidic crystalline microporous materials can range from 0.01 to 20 weight percent. The lead modifier content of the non-acidic crystalline microporous materials can range from 0.01 to 20 weight percent. Practically, the modifier content will range from 0.1 to 10 weight percent.

The non-acidic crystalline microporous modifier containing materials of the invention include zeolites characterized by Si/Al ratios of at least 2. However, the silica:alumina ratio of the zeolite can be up to 1000, or greater. In a preferred embodiment the aluminum content of these materials is less than 0.1 weight percent and more preferably less than 0.02 weight percent.

The non-acidic crystalline microporous thallium or lead modifier containing material of the invention can contain other elements including boron, iron, chromium and gallium. The content of these other elements in the non-acidic crystalline microporous material containing silicates can range from 0 to 10 weight percent.

The non-acidic crystalline microporous materials of the invention, described herein, are crystalline in the sense that they are identifiable as isostructural with zeolites by X-ray powder diffraction pattern. The crystalline microporous material has an X-ray diffraction pattern which corresponds to a zeolite, SAPO, ALPO, etc.

In a preferred embodiment the pore size of the non-acidic microporous crystalline containing materials ranges from about 5 to about 8 Angstroms. In a preferred embodiment the microporous crystalline material containing modifier exhibits the structure of ZSM-5, by X-ray diffraction pattern. The X-ray diffraction pattern of ZSM-5 has been described in U.S. Pat. No. 3,702,886 and RE 29,948 each of which is incorporated by reference herein.

The compositions of the invention do not exhibit any appreciable acid activity. These catalysts would meet the criteria of the non-acidic catalysts described by Davis and Venuto, J. CATAL. Vol. 15, p.363 (1969). Thus, a non-equilibrium mixture of xylenes are formed from either n-octane or each individual methylheptane isomer, with the octane yielding more o-xylene and 2-methyl-heptane yielding mostly m-xylene, at conversions between 10 and 60%.

When, as in embodiments herein, the dehydrogenation metal containing non-acidic microporous crystalline material exhibits an X-ray diffraction pattern of a zeolite, at least some of the dehydrogenation metal may be intrazeolitic, that is, some of that metal is within the pore sturcture of the crystal, although some of that metal can be on the surface of the crystal. A test for determining whether, for example, Pt is intrazeolitic or extrazeolitic in the case of ZSM-5 is reported by R. M. Dessau, J. CATAL. Vol. 89, p. 520 (1984). The test is based on the selective hydrogenation of olefins.

Compositions of the invention used in catalysis decrease the hydrogen content of the reactant to produce a product having the same number of carbon atoms as the number of carbon atoms in the reactant. By comparison modifier-free counterparts of these compositions also catalyzed hydrogenolysis of paraffins, e.g., to methane, as a major competing side reaction; and, accordingly, the latter compositions exhibit decreased selectivity for the aromatization of paraffins but increased selectivity for $C_1$–$C_5$ paraffin production. Some of the aforementioned catalysts were screened for hexane and heptane aromatization at 538° C. in the presence of nitrogen diluent. The results are shown in Table A below in which the crystalline silicate employed exhibited the X-ray diffraction pattern of a ZSM-5.

TABLE A

| Heptane Aromatization over Non-acidic Pt/ZSM-5 | | | | |
|---|---|---|---|---|
| Modifier | % Conv. | Toluene Sel. | Benzene Sel. | CH$_4$Sel. |
| Sn | 99.3 | 95.0% | 1.5% | 0.4% |
| In | 98.2 | 92.7% | 1.8% | 0.5% |
| Pb | 98.7 | 95.4% | 1.1% | 0.4% |
| Tl | 99.6 | 85.7% | 6.7% | 1.7% |
| — | 96.3 | 40.9% | 19.4% | 9.3% |
| B | 94.7 | 30.2% | 32.8% | 20.7% |
| Cr | 95.5 | 44.4% | 20.4% | 3.4% |
| Ti | 96.1 | 31.8% | 32.6% | 19.7% |

TABLE A-continued

| Heptane Aromatization over Non-acidic Pt/ZSM-5 | | | | |
|---|---|---|---|---|
| Modifier | % Conv. | Toluene Sel. | Benzene Sel. | CH$_4$Sel. |
| Sc | 96.3 | 38.9% | 40.6% | 16.0% |
| Au | 90.7 | 21.1% | 45.1% | 20.8% |
| Ni | 94.3 | 42.4% | 19.7% | 7.2% |
| Ge | 96.3 | 47.0% | 19.9% | 6.6% |
| Zr (470° C.) | 96.8 | 49.0% | 16.3% | 7.9% |

(a) 30 torr n-heptane in N$_2$ at 538° C. and 1 atm.; selectivities on H$_2$-free weight basis.

By comparison, the non-acidic platinum catalyst prepared from either thallium/ZSM-5 or lead/ZSM-5 provided much higher aromatics selectivity than all the other catalysts examined in Table A except for Sn and In. Toluene selectivity from heptane was greater than 85% at 99% conversion (H$_2$ free carbon basis).

For comparison purposes, it should be noted that over dual functional platinum on acidic alumina reforming catalysts, the rate of heptane cracking to $C_6^-$ was twice the rate of dehydrocyclization. Cf J. H. Sinfelt, "Bimetallic Catalysts", J. Wiley, New York; p. 141 (1983).

The catalysts, including Pt/B-ZSM-5 and Pt/high silica:alumina ratio as well as those others enumerated in the Table did not show any appreciable acid activity, in that platinum chemistry dominated. Significant metal-catalyzed aromatization was observed; however hydrogenolysis to methane constituted a major competing side reaction. The highest toluene selectivity observed was 50–55%, and in most cases that selectivity was significantly lower. This is in sharp contrast to the aromatic product selectivity of the platinum/thallium/ZSM-5 and platinum/lead/ZSM-5. The cause for this difference in platinum behavior is not clear.

SYNTHESIS OF THE COMPOSITIONS

The crystalline materials containing lead or thallium, the modifier, can be made in various ways. Lead or thallium modifier can be incorporated during synthesis or post-synthesis; and the materials can be prepared either by stepwise or simultaneous incorporation of the modifier and the hydrogenation/dehydrogenation function to the crystallization reaction product. The dehydrogenation function can be first introduced to the synthesis product with subsequent modifier incorporation, or vice versa. Stepwise preparation includes techniques of cocrystallization, impregnation, or exchange. Crystallization can be undertaken in a two phase system described in commonly assigned Ser. No. 878,555, filed June 26, 1986. Other elements such as boron, iron, chromium, gallium, can also be included. Simultaneous incorporation includes the combination of the modifier with the dehydrogenation/hydrogenation function during synthesis (i.e., crystallization) or simultaneously after synthesis of the crystalline material.

A modifier-free precursor material can be treated with sources of the modifier at elevated temperatures. Such treatments can be conducted so that that the source is either in the gaseous or the liquid phase including the aqueous phase. Alternatively, a thallium or lead free crystalline reactant can simply be impregnated with a thallium or lead source and then calcined at temperatures above 400° C. The crystalline reactants may have high silica:alumina ratios or contain other elements such as boron, chromium, iron, and gallium. Reactants and products containing 0.1 weight percent or less aluminum are the preferred embodiments of the examples. In materials of the invention, all cation-exchangeable sites are occupied by cations other than hydrogen and other than hydrogen precursors, such as $NH_4^+$. Specifically, such sites are occupied by $Na^+$, $K^+$, $Cs^+$, $Ca^+$, $Mg^{++}$, $Ba^{++}$, $Sr^{++}$, or admixtures thereof. The alkali metals serve to neutralize any acidity due to framework aluminum. The source of alkali metal cation can derive from cations incorporated during synthesis, in excess of the aluminum content thereof. Alternatively, one can treat the final product with a basic solution of an alkali metal hydroxide as a final step prior to use, as described for example in U.S. Pat. No. 4,652,360.

The non-acidic, crystalline, microporous, modifier and dehydrogenation metal containing materials of the invention can be combined with a matrix or binder material to render them attrition resistant and more resistant to the severity of the conditions to which they will be exposed during use in hydrocarbon conversion applications. The combined compositions can contain 1 to 99 weight percent of the materials of the invention based on the combined weight of the matrix (binder) and material of the invention. When used in dehydrogenation and/or dehydrocyclization, the material of the invention will preferably be combined with non-acidic matrix or binder materials. A preferred matrix or binder material would be silica, when the materials of the invention are used in dehydrogenation/hydrogenation or dehydrocyclization.

USE OF THE CATALYST COMPOSITION

These compositions of the invention exhibit high selectivity for dehydrogenation and/or dehydrocyclization and reforming, which is evidenced by the examples. In dehydrogenation, dehydrocyclization and reforming processes, the microporous crystalline thallium and lead containing silicates are combined with reforming metals, or dehydrogenation/hydrogenation metals.

CATALYTIC DEHYDROGENATION AND DEHYDROCYCLIZATION

In accordance with the invention catalytic dehydrogenation comprises contacting an aliphatic, with the catalyst composition of the invention to produce a corresponding unsaturated analog together with hydrogen. The catalytic dehydrogenation exhibits high selectivity with respect to production of said unsaturated analog, with substantially little, if any, selectivity for products of hydrogenolysis (cracking).

In dehydrogenation the feedstocks comprise at least one unsubstituted or substituted straight or branched chain aliphatic compound in which the aliphatic moiety has two to five carbon atoms. In accordance with the invention, dehydrogenation of the aliphatic moiety occurs to yield the unsaturated analog. When the aliphatic moiety is substituted, the substituents can be substituted or unsubstituted aryls. The class of reactants includes alkanes of 2 to 5 carbon atoms including ethane, propane, butane, isobutane, pentane and 2 methylbutane. Dehydrogenation of those respective alkane reactants will yield ethylene, propylene, butene, isobutene, pentene and isopentene.

The class of reactants includes olefins of 2 to 5 carbon atoms such as ethylene, butene, pentene, and isopentene. Dehydrogenation of ethylene will produce acetylene; dehydrogenation of butene will produce butadiene and dehydrogenation of methyl butene will produce isoprene.

The class of reactants employed in the dehydrogenation of the invention includes aromatic substituted aliphatics. Preferably, the aliphatic group of the aryl substituted aliphatic contains less than four carbon atoms and more preferably more than 1 carbon atom. The aryl substituted aliphatic reactants embrace unsubstituted arylaliphatics and alkyl substituted aryl aliphatics and; similarly, each of the alkyls of said alkyl substituted alkylaryls contains preferably less than 4 carbon atoms. By way of illustration reactants such as ethyl benezene, diethylbenzene, ethyl toluene, and cumene are representative of these compounds. On dehydrogenation in accordance with the invention, ethyl benzene will produce styrene; ethyl toluene will produce p-methylstyrene; cumene, isopropenylbenzene; and diethylbenzene, divinylbenzene.

In accordance with the invention, catalytic dehydrogenation conditions include pressures varying from subatmospheric, to atmospheric to greater than atmospheric. Preferred pressures range from 0.1 atmospheres to atmospheric. However, pressures up to 500 psig can be employed. The dehydrogenation is conducted at elevated temperatures ranging from 400° C. to 700° C. and most preferably from 300° C. to 600° C. Reactor inlet $H_2$/feed ratios are 5 or less; even at reactor inlet ratios of zero (0), there will be a hydrogen partial pressure in the reactor because hydrogen is a by-product of dehydrogenation. The liquid hourly space velocity is 0.1 to 50, preferably 0.2 to 10.

Under these conditions, the catalytic dehydrogenation of the invention exhibits reduced selectivity for hydrogenolysis or for isomerization. The unsaturated product of the process of the invention is produced with higher selectivity than the selectivity of competing processes to produce homologs of lower carbon atom number than the reactant and to produce isomers under the same conditions.

Dehydrogenation may be conducted in the presence or absence of purposefully added hydrogen and in the presence of diluents inert to conditions of the catalytic dehydrogenation such as nitrogen and methane. In particular, dehydrogenation can be advantageously conducted at low hydrogen pressure.

Dehydrocyclization in accordance with the invention comprises contacting an aliphatic of at least six (6) carbon atoms with the catalytic composition comprising a dehydrogenation/hydrogenation metal which can be any Group VIII metal, preferably platinum.

The feedstocks charge to the new reforming process can be straightrun, thermal, or hydrocracker naphtha. Preferably, for high increases in the aromatic content and high octane numbers of the reformate, the charge to the reformer is a naphtha rich in $C_6$ and $C_7$ paraffins; these are generally difficult to reform selectively using conventional catalysts (such as chlorided Pt-alumina). Naphthas can be obtained by separating the charge into two fractions: a light naphtha and a heavy naphtha. Conventionally such separation is by distillation. The boiling range of the light naphtha is from about 80° F. to about 280° or 300° F. and the boiling range of the heavy naphtha will be from 280° or 300° F. The light naphtha will be rich in $C_6$–$C_{10}$ paraffins, and specifically $C_6$ and $C_7$ paraffins. In accordance with one embodiment when the light naptha is reformed in accordance with the invention, the heavy naphtha will be processed by conventional reforming. The naphtha fractions may be hydrotreated prior to reforming. Initial hydrotreating of a hydrocarbon feed serves to convert sulfur, nitrogen and oxygen derivatives of hydrocarbon to hydrogen sulfide, ammonia, and water while depositing metal contaminant from hydrodecomposition of any organometal compounds. Where desired, interstage processing of the effluent from the hydrotreating zone may be effected. Such interstage processing may be undertaken, for example, to provide additional hydrogen, to add or remove heat or to withdraw a portion of the hydrotreated stream for treatment which need not be reformed. Hydrotreating of the heavy naphtha fraction may be essential, prior to reforming in a conventional reforming process. Suitably, the temperature in the hydrotreating catalyst bed will be within the approximate range of 550° F. to 850° F. The feed is conducted through the bed at an overall space velocity between about 0.1 and about 10 and preferably between 0.2 and about 2, with hydrogen initially present in the hydrotreating zone in an amount between about 1000 and 10,000 standard cubic feet per barrel of feed, corresponding to a ratio of between about 2.4 and about 24 moles of hydrogen per mole of hydrocarbon. The catalyst may be any of the known hydrotreating catalysts, many of which are available as staple articles of commerce. These hydrotreating catalysts are generally metals or metal oxides of Group VIA and/or Group VIII deposited on a solid porous support, such as silica and/or metal oxides such as alumina, titania, zirconia or mixtures thereof. Representative Group VIA metals include molybdenum, chromium and tungsten and Group VIII metals include nickel, cobalt, palladium and platinum. These metal components are deposited, in the form of metals or metal oxides, on the indicated supports in amounts generally between about 0.1 and about 20 weight percent.

When dehydrogenation, dehydrogenation or reforming is undertaken over the catalyst in accordance with the invention, the temperature can range broadly from 800° F. to 1100° F., generally being greater than about 900° F., preferably being 900° F. (482° C.) to 1050° F.; the pressure will be from about 1 atmosphere to 500 psig, preferably from 30 psig to 250 psig; inlet $H_2$/hydrocarbon can be 5 or less, even zero (0) (because of hydrogen production during reforming, there will be a hydrogen partial pressure in the unit); while the LHSV (liquid hourly space velocity) can be 0.1 to 20, preferably 0.1 to 10.

Selectivity and aging characteristics at low hydrogen partial pressures may be superior to conventional non-zeolitic reforming catalysts. With these catalysts, the reforming process can be run in the absence of added hydrogen, and preferably even, in the presence of diluents such as nitrogen, methane, propane, pentanes, and $C_6$-$C_8$ aromatics.

Reforming of the heavy naphtha fraction, boiling range of up to 650° F. can be undertaken separately from the light naphtha fraction, by conventional reforming. As discussed above, conventional reforming may be semi-regenerative, cyclic or continuous. Process conditions in reforming include pressures of about 0 to 500 psig, preferably, the pressures used herein range from 0-250 psig and most preferably are 0-150 psig; temperatures of 800° to 1100° F.; $H_2$/HC molar ratios of 0 to 20:1 preferably of about 2:1 to about 6:1; LHSV of 0.1 to 20 hr$^{-1}$. Conventional reforming catalysts for this stage can include conventional reforming hydrogenation/dehydrogenation metals on aluminas. Those reforming hydrogenation/dehydrogenation metals include: platinum, platinum-rhenium; platinum with iridium, rhenium, rhodium or admixtures thereof; or platinum/tin. These hydrogenation/dehydrogenation metal combinations are on alumina and are chlorided; generally they are presulfided prior to use on feeds containing less than about 1 ppm sulfur.

EXAMPLE 1

Thallium ZSM-5 silicate synthesis was undertaken as follows: A solution was prepared by dissolving 0.85 g TlNO$_3$ in 170.6 g deionized water and then by adding 2.05 g NaOH pellets. After all the base had dissolved, 6.38 g tetrapropylammonium bromide (TPABr) was added. The resulting solution was transferred to a 300 ml stainless steel autoclave and 16.0 g of silica gel (SPEX Ind.) was stirred into the solution. The hydrogel produced can be described by the following mole ratios:

$SiO_2/Tl_2O:H_2O/SiO_2:OH-/SiO_2:Na+/SiO_2:TPA+/SiO_2$

| 150 | 40 | 0.20 | 0.21 | 0.10 |

The hydrogel was heated in the autoclave for 4 days at 160° C., with stirring at 400 rpm. The product was filtered, washed and dried. X-ray diffraction analysis indicated it to be 100% crystalline ZSM-5.

Elemental analysis indicated the presence of 8.26% C., 1.88% H, 0.74% N, 0.34% Na, 4.33% Tl, 80.65% $SiO_2$, and 0.0095% Al in the ZSM-5 product.

EXAMPLE 2

Catalyst preparation was undertaken as follows: The as-synthesized thallium silicate was calcined, first in nitrogen and then in air, at 520° C. The calcined zeolite contained 2.43% Tl, 38 ppm Al, and 43.15% Si.

Platinum was incorporated by ion exchange with Pt(NH$_3$)$_4$Cl$_2$ (15 mg/g zeolite) at room temperature. TGA ammonia titration in hydrogen indicated the presence of 0.67% Pt. The platinum-containing zeolite was then calcined in oxygen to 350° C. where it was maintained for one hour at 0.5° C./min.

EXAMPLE 3

The "non-acidic" nature of the catalyst of Example 2 was confirmed by its ability to aromatize n-heptane to toluene in high yield. At 538° C. and 30 torr heptane in nitrogen, toluene was formed in 83–88% selectivity at a conversion of 99+%. Total yield of benzene plus toluene was greater than 90%.

EXAMPLE 4

The above catalyst of Example 2 was used to study the reforming of a hydrotreated Arab light naphtha, b.p. 180°–250° F. The reaction was run at 538° C. at atmospheric pressure at 1.8 WHSV and a N$_2$/HC ratio of 2.2. The results obtained are shown below:

| | Feed | Product | % Converted |
|---|---|---|---|
| $C_1$—$C_4$ | 0 | 0.4 | |
| Methylpentanes | 16.5 | 11.6 | 30% |
| n-Hexane | 24.2 | 12.2 | 50% |
| Methylhexanes | 15.6 | 11.8 | 24% |
| n-Heptane | 17.1 | 7.2 | 58% |
| Benzene | 2.1 | 14.0 | |
| Toluene | 3.2 | 11.5 | |

Preliminary screening of the thallium-modified non-acidic Pt/ZSM-5 catalyst described above for the reforming of a hydrotreated Arab light naphtha, b.p. 180°–250° F., indicated highly selective aromatics formation together with very low $C_1$–$C_4$ gas production. At 538° C., atmospheric pressure, 1.8 WHSV, and a $N_2$:HC ratio of 2.2, preferential conversion of the normal paraffins to benzene and toluene was observed, as shown above.

EXAMPLE 5

Lead-containing ZSM-5 was synthesized. A solution A was prepared by dissolving 3.31 g Pb(NO$_3$)$_2$ in 338.8 g de-ionized water. A solution B was prepared by dissolving 12.4 g NaOH in 300 g de-ionized water. 23.94 g TPA bromide was then dissolved in solution B, which was then poured into solution A. 60.0 g silica gel (SPEX Ind.) was placed in a 1-liter stainless steel autoclave. The solution was now transferred to the autoclave, and the mixture was stirred for two minutes before sealing the autoclave. Stirring and heating were begun immediately. The composition of the hydrogel formed is described by the following mole ratios:

$SiO_2/Pb:H_2O/SiO_2:OH^-/SiO_2:Na^+/SiO_2:TPA^+/SiO_2$

90:40:0.30:0.34:0.10

The zeolite crystallization was carried out at 160° C. with stirring at 400 rpm for 4 days. The product ZSM-5 analyzed for 7.96% C, 0.7% N, 0.97% Na, 4.0% Pb, 86.48% ash, and 235 ppm Al$_2$O$_3$. Platinum incorporation was similar to that in Example 2.

EXAMPLES 5–12

The preparation of the borosilicate ZSM-5 has been described. High silica:alumina ZSM-5 samples containing the elements: chromium, titanium, scandium, nickel, gold, germanium, and zirconium were synthesized in a manner analogous to that used to prepare Tl-ZSM-5, described above. The synthesis conditions are show in in Table 1 below:

TABLE 1

| | | Synthesis of Metal-Containing ZSM-5 | | | | | |
|---|---|---|---|---|---|---|---|
| | Metal | Mixture Composition (Mole Ratio) | | | | | |
| Example No. | (M) Salt | SiO$_2$/M | H$_2$O/SiO$_2$ | OH$^-$/SiO$_2$ | Na$^+$/SiO$_2$ | TPA$^+$/SiO$_2$ | Time Days |
| 5 | Pb(NO$_3$)$_2$ | 90 | 40 | 0.30 | 0.34 | 0.10 | 4 |
| 6 | CrCl$_3$.6H$_2$O | 75 | 40 | 0.30 | 0.35 | 0.10 | 3 |
| 7 | TiCl$_4$ | 150 | 40 | 0.30 | 0.33 | 0.10 | 5 |
| 8 | Sc(NO$_3$)$_3$.4H$_2$O | 75 | 40 | 0.20 | 0.21 | 0.10 | 4 |
| 9 | Ni(NO$_3$)$_3$.6H$_2$O | 75 | 40 | 0.30 | 0.27 | 0.10 | 3 |
| 10 | Au(OH)$_3$ | 75 | 40 | 0.30 | 0.35 | 0.10 | 3 |
| 11 | GeCl$_4$ | 75 | 40 | 0.20 | 0.25 | 0.10 | 5 |
| 12 | Zr(NO$_3$)$_4$ | 75 | 48 | 0.26 | 0.31 | 0.10 | 3 |

The synthesized zeolites all contained less than 0.06% Al and more than 0.4% Na. The final platinum-containing catalysts contained 0.57–0.80% Pt.

EXAMPLE 13

The apparent "alpha activity" of the non-acidic platinum containing zeolites was measured using the standard alpha apparatus in either helium or hydrogen over a period of 1–3 hours. The relative hexane conversion activites of the various Pt/ZSM-5 catalysts are shown in Table 2 below:

TABLE 2

| Relative Hexane Conversion Activities for Various Pt/ZSM-5 Catalysts | | | |
|---|---|---|---|
| Catalyst | % Pt | % M | Activity[a] |
| hi Si | 0.6 | — | 746 |
| Sn | 1.5 | 2.7 | 1013 |
| In | 0.9 | 2.5 | 320 |
| Tl | 0.7 | 4.5 | 94 |
| Pb | 1.4 | 4.5 | 193 |
| Cr | 0.6 | 0.3 | 605 |
| Ti | 0.8 | 1.0 | 865 |
| Sc | 0.6 | 0.9 | 169 |
| Au | 0.7 | 3.9 | 763 |
| Ni | 0.8 | 1.5 | 968 |
| Ge | 0.9 | 0.4 | 691 |
| Zr | 0.6 | 3.1 | 398 |

[a]"Apparent alpha" at 538° C. in He after 1 hour on stream.

EXAMPLE 14

The catalysts of Table 2 were used in heptane aromatization reactions which were conducted at 538° C. in a down-flow glass reactor, and the reactor effluents were analyzed directly by on-line gas chromatography. Heptane was introduced into the reactor in a nitrogen stream passing through a vaporizer containing n-heptane at 15°–20° C.

The aromatization reaction of n-heptane at 538° C. and 30 torr in nitrogen was chosen to evaluate and characterize various Pt/ZSM-5 catalysts. In general, Pt/ZSM-5 catalysts fell into three broad classes: (1) acidic, producing low overall yields of aromatics and high yields of $C_3$–$C_4$ hydrocarbons; (2) non-acidic, producing significant amounts of both benzene and toluene together with considerable methane; and (3) non-acidic bimetallic (i.e., metal-modified), characterized by extremely high yields of toluene with low methane formation.

The first class was exemplified by a Pt/H-Ga-ZSM-5 material prepared by ion-exchanging out all sodium ions prior to platinum incorporation. Under the test conditions, $C_5^-$, selectivities, mainly propylene and butenes, were greater than 70% while total aromatic selectivities were less than 20%.

The second class was exemplified by non-acidic Pt/ZSM-5 catalysts prepared from a very high silica/alumina ZSM-5 or from a low aluminum content borosilicate (see Table A).

Aromatic selectivities of the reactions catalyzed by Table 2 compositions and reported in Table A were in the 62–66% range with benzene frequently exceeding the toluene produced. The major $C_5^-$ product formed was methane, which was produced in greater than 30% selectivity at high heptane conversions.

Non-acidic Pt/ZSM-5 catalysts, synthesized in the presence of and containing the following elements:

chromium, titanium, scandium, gold, nickel, germanium, or zirconium, also fell into this second category as shown in Table A. Some variations in selectivities were observed (primarily as a function of conversion); however, in no case was the yield of toluene greater than 50–55%. Methane was again the prime light gas produced over these catalysts.

In contrast to these bimetallic catalysts, non-acidic bimetallic Pt/ZSM-5 containing the modifiers: indium, tin, thallium, or lead, exhibited dramatically enhanced toluene selectivities approaching 95% or better (on a mole basis).

The improved aromatization selectivity of these catalysts is due to suppression of hydrogenolysis by platinum, especially methane formation. Reduction in hydrogenolysis selectivity of various metal catalysts by alloying with other metals so as to form more selective mixed clusters has been reported in the literature. J. H. Sinfelt, "Bimetallic Catalysts", J. Wiley, New York, 1983; L. Guczi, in Stud. Surf. Sci, Cat., Elsevier, Amsterdam, 1986, vol. 29, p.547; J. Volter, in Stud. Surf. Sci. Cat., Elsevier, Amsterdam, 1986, vol. 27, p.337.

What is claimed is:

1. A catalyst comprising a non-acidic composition comprising of
   a dehydrogenation metal; and
   a non-acidic microporous crystalline material, comprising thallium or lead, wherein thallium or lead is present in an amount which ranges from 0.01 to 20 weight percent, of said material.

2. The catalyst of claim 1, wherein the dehydrogenation metal is a platinum group metal.

3. The catalyst of claim 1, wherein the dehydrogenation metal is platinum.

4. The catalyst of claim 1, wherein the dehydrogenation metal is present in an amount effective to catalyze dehydrogenation.

5. The catalyst of claim 1, wherein the microporous crystalline material has pores the size of which ranges from 5–8 Å.

6. The composition of claim 1, wherein the material is a zeolite.

7. The catalyst of claim 1, which contains aluminum in an amount less than 0.1 weight percent.

8. The composition of claim 5, wherein the material has the X-ray diffraction pattern of ZSM-5.

9. A catalyst comprising a non-acidic composition consisting of a dehydrogenation metal; and
   a non-acidic microporous crystalline material, comprising thallium in an amount which ranges from 0.01 to 20 weight percent, of said material.

10. The catalyst of claim 9, wherein the dehydrogenation metal is a platinum group metal.

11. The catalyst of claim 9, wherein the dehydrogenation metal is platinum.

12. The catalyst of claim 9, wherein the dehydrogenation metal is present in an amount effective to catalyze dehydrogenation and/or dehydrocyclization.

13. The catalyst of claim 9, wherein the microporous cystalline material has pores the size of which ranges from 5–8 Å.

14. The composition of claim 9, wherein the material is a zeolite.

15. The catalyst of claim 9, which contains aluminum in an amount less than 0.1 weight percent.

16. The composition of claim 13, wherein the material has the X-ray diffraction pattern of ZSM-5.

17. A catalyst comprising a non-acidic composition consisting of a dehydrogenation metal; and
   a non-acidic microporous crystalline material, comprising lead in an amount which ranges from 0.01 to 20 weight percent, of said material.

18. The catalyst of claim 17, wherein the dehydrogenation metal is a platinum group metal.

19. The catalyst of claim 17, wherein the dehydrogenation metal is platinum.

20. The catalyst of claim 17, wherein the dehydrogenation metal is present in an amount effective to catalyze dehydrogenation and/or dehydrocyclization.

21. The catalyst of claim 17, wherein the microporous cystalline material has pores the size of which ranges from 5–8 Å.

22. The composition of claim 17, wherein the material is a zeolite.

23. The catalyst of claim 17, which contains aluminum in an amount less than 0.1 weight percent.

24. The composition of claim 21, wherein the material has the X-ray diffraction pattern of ZSM-5.

* * * * *

UNITED STATES PATENT AND TRADEMARK OFFICE
CERTIFICATE OF CORRECTION

PATENT NO. : 4,931,416

DATED : June 5, 1990

INVENTOR(S) : Dessau & Valyocsik

It is certified that error appears in the above-identified patent and that said Letters Patent is hereby corrected as shown below:

Column 11, line 25, "comprising" should read "consisting"

Signed and Sealed this

Fifteenth Day of October, 1991

Attest:

HARRY F. MANBECK, JR.

*Attesting Officer*  *Commissioner of Patents and Trademarks*